(12) United States Patent
Jiang et al.

(10) Patent No.: US 11,925,784 B2
(45) Date of Patent: Mar. 12, 2024

(54) INSULIN INJECTION DEVICE

(71) Applicant: INNOMD MEDICAL TECHNOLOGY SERVICES CO. LTD., Jiangsu (CN)

(72) Inventors: Feng Jiang, Jiangsu (CN); Haotian Jiang, Jiangsu (CN)

(73) Assignee: INNOMD MEDICAL TECHNOLOGY SERVICES CO. LTD., Jiangsu (CN)

( * ) Notice: Subject to any disclaimer, the term of this patent is extended or adjusted under 35 U.S.C. 154(b) by 908 days.

(21) Appl. No.: 16/932,471

(22) Filed: Jul. 17, 2020

(65) Prior Publication Data

US 2020/0345928 A1 Nov. 5, 2020

Related U.S. Application Data

(63) Continuation of application No. PCT/CN2018/121415, filed on Dec. 17, 2018.

(30) Foreign Application Priority Data

Jan. 19, 2018 (CN) .......................... 201810054424.4

(51) Int. Cl.
*A61M 5/142* (2006.01)
*A61B 5/00* (2006.01)
(Continued)

(52) U.S. Cl.
CPC ....... *A61M 5/14244* (2013.01); *A61B 5/0075* (2013.01); *A61B 5/0084* (2013.01);
(Continued)

(58) Field of Classification Search
CPC ............ A61M 5/14244; A61M 5/1723; A61M 5/3155; A61M 5/31581;
(Continued)

(56) References Cited

U.S. PATENT DOCUMENTS

| 4,280,494 A | 7/1981 | Cosgrove, Jr. et al. |
| 7,803,129 B2 * | 9/2010 | Brouillette .......... A61M 5/3007 128/200.14 |

(Continued)

FOREIGN PATENT DOCUMENTS

| CN | 101132821 | 2/2008 |
| CN | 101646470 | 2/2010 |

(Continued)

OTHER PUBLICATIONS

International Search Report issued for International Patent Application No. PCT/CN2018/121415, dated Mar. 15, 2019, 7 pages including English translation.

*Primary Examiner* — Dung T Ulsh
(74) *Attorney, Agent, or Firm* — Hamre, Schumann, Mueller & Larson, P.C.

(57) ABSTRACT

This invention provides an insulin injection device, comprising: a wearable module, a detection module and a drug administration module, wherein the wearable module is used for fixing the detection module and the drug administration module to a body of a user; the detection module is used for detecting a blood glucose concentration of the user, determining a dose of required insulin according to the blood glucose concentration, generating a corresponding drug administration instruction according to the dose of the required insulin, and sending the drug administration instruction to the drug administration module; and the drug administration module is used for storing the insulin and injecting a corresponding dose of insulin into the body of the user according to the drug administration instruction. The device can bring convenience to patients regarding usage.

13 Claims, 6 Drawing Sheets

(51) Int. Cl.
*A61B 5/145* (2006.01)
*A61M 5/172* (2006.01)
*A61M 5/315* (2006.01)

(52) U.S. Cl.
CPC ....... *A61B 5/14532* (2013.01); *A61M 5/1723* (2013.01); *A61M 5/3155* (2013.01); *A61M 5/31581* (2013.01); *A61M 2005/14208* (2013.01); *A61M 2005/1726* (2013.01)

(58) Field of Classification Search
CPC  A61M 2005/14208; A61M 2005/1726; A61B 5/0075; A61B 5/0084; A61B 5/14532
See application file for complete search history.

(56) References Cited

U.S. PATENT DOCUMENTS

| | | | |
|---|---|---|---|
| 7,833,189 B2 | 11/2010 | Hunter et al. | |
| 2002/0111600 A1* | 8/2002 | Cormier | A61N 1/303 606/186 |
| 2003/0104982 A1 | 6/2003 | Wittmann et al. | |
| 2010/0106076 A1 | 4/2010 | Nisato et al. | |
| 2010/0256593 A1* | 10/2010 | Yodfat | A61M 5/14248 600/347 |

FOREIGN PATENT DOCUMENTS

| | | |
|---|---|---|
| CN | 107174257 | 9/2017 |
| CN | 108245742 | 7/2018 |

* cited by examiner

INSULIN INJECTION DEVICE

CROSS REFERENCE TO RELATED APPLICATIONS

This application is a continuation of international application No. PCT/CN2018/121415, filed on Dec. 12, 2018, the disclosures of which are hereby incorporated by reference.

FIELD OF THE INVENTION

The present invention relates to the field of mechanical technologies, and more particularly, to an insulin injection device.

BACKGROUND

Diabetes is a metabolic disease characterized by hyperglycemia, and the hyperglycemia is caused by defect of insulin secretion or damage of biological action, or both of them. The diabetes brings great pain to patients.

Drug treatment is generally used to control the diabetes in current diabetes treatment methods, wherein insulin injection is a main treatment method among various drug treatment methods.

When insulin is used to treat the diabetes, diabetic patients are injected with the insulin before or after meals according to a doctor's advice to control the increase of blood glucose in a body after meals. Although the diabetic patients are injected with the insulin before or after meals, the amount and type of food taken by the diabetic patients in each meal are different. When the insulin is injected according to a same standard, the diabetic patients are easy to have hypoglycemia or the hyperglycemia. Moreover, the patients also need to remember an injection time of the insulin. Therefore, the current diabetes treatment methods cause great inconvenience to the patients.

SUMMARY OF THE INVENTION

The embodiment of the present invention provides an insulin injection device, which can bring convenience to patients regarding usage.

The embodiment of the present invention provides the insulin injection device, comprising: a wearable module, a detection module and a drug administration module, wherein:
the wearable module is respectively connected to the detection module and the drug administration module, and can be used for fixing the detection module and the drug administration module to a body of a user;
the detection module is used for detecting a blood glucose concentration of the user by a Raman spectrum, determining a dose of required insulin according to the blood glucose concentration, generating a corresponding drug administration instruction according to the dose of the required insulin, and sending the drug administration instruction to the drug administration module; and
the drug administration module is used for storing the insulin and injecting a corresponding dose of insulin into the body of the user according to the drug administration instruction.

Optionally, the detection module comprises a light emitter, a light receiver and a processor;
the light emitter is used for emitting detection light to a subcutaneous tissue of the user through a skin of the user;
the light receiver is used for receiving scattered light formed by inelastic scattering of the detection light, and forming the corresponding Raman spectrum according to the scattered light; and
the processor is used for determining the blood glucose concentration of the user according to the Raman spectrum formed by the light receiver.

Optionally, the processor is used for calculating the blood glucose concentration of the user according to the Raman spectrum through the following formula:

$$G = \left(1 + e^{\frac{\int(Q_1 t)dt - \int(Q_2 t)dt}{\int(Q_2 t)dt + \int(Q_1 t)dt}}\right) \cdot \int(Q_2 t)dt$$

wherein, G represents the blood glucose concentration of the user, $Q_1$ represents an intensity of scattered light formed by the detection light in a skin layer of the user, $Q_2$ represents an intensity of scattered light formed by the detection light in a subcutaneous tissue layer of the user, and t represents Raman shift of the Raman spectrum.

Optionally, the detection module further comprises a first skin tensioner;
the first skin tensioner comprises at least two fan rings, and the at least two fan rings can form an annular structure; one side of each fan ring contacting with the skin of the user is provided with an anti-skid layer; and
the first skin tensioner is used for driving the at least two fan rings to move in a direction away from a center of the annular structure before the light emitter emits the detection light, so as to tension the skin of the user in an area surrounded by the at least two fan rings.

Optionally, the drug administration module comprises at least one air tank, a needleless injector, a drug administration mechanism and a drug storage mechanism;
the drug administration mechanism is used for obtaining the corresponding dose of insulin from the drug storage mechanism according to the drug administration instruction, and adding the obtained insulin into the needleless injector;
the at least one air tank is used for filling high-pressure driving gas into the needleless injector after the insulin is added into the needleless injector by the drug administration mechanism; and
the needleless injector is used for injecting the insulin into the subcutaneous tissue of the user in a form of liquid flow under driving of the high-pressure driving gas.

Optionally, the needleless injector comprises a cylinder body, a piston, a reset spring and a piston nozzle;
the cylinder body has a cylindrical structure, a first end of the cylinder body is provided with at least one air inlet, and a second end of the cylinder body is provided with the piston nozzle, wherein the air inlet is connected to the air tank through a pipeline;
the piston is located inside the cylinder body, and can reciprocate along an axial direction of the cylinder body;
the reset spring is located inside the cylinder body and between the piston and the piston nozzle;
the piston is used for moving in a direction close to the piston nozzle along an axis of the cylinder body under a driving action of the high-pressure driving gas and impacting a piston rod of the piston nozzle, so as to eject the insulin in the piston nozzle in the form of liquid flow; and the reset spring is used for driving the piston to move in a direction away from the piston nozzle along the axis of the cylinder body to a free position after the piston moves in the direction close to the piston nozzle along the axis of the cylinder body to a limit position.

Optionally, the drug administration module comprises at least two air tanks; and at least two air inlets are evenly arranged at the first end of the cylinder body, and each air inlet is connected to one air tank through the pipeline.

Optionally, the drug storage mechanism has a wheeled structure, at least two tubular drug storage bins are arranged on an inner wall of the wheeled structure, each tubular drug storage bin can store a unit dose of insulin, and the wheeled structure can rotate along the axis under driving of the drug administration mechanism; and the drug administration mechanism has a rod-shaped structure, is used for driving the drug storage mechanism to rotate according to the drug administration instruction, and sequentially enters at least one drug storage bin, so as to push the insulin stored in each drug storage bin into the needleless injector.

Optionally, the drug administration module further comprises a second skin tensioner;

the second skin tensioner comprises at least two fan rings, and the at least two fan rings can form an annular structure; one side of each fan ring contacting with the skin of the user is provided with an anti-skid layer; and the second skin tensioner is used for driving the at least two fan rings to move in a direction away from a center of the annular structure before the needleless injector injects the insulin into the subcutaneous tissue of the user, so as to tension the skin of the user in an area surrounded by the at least two fan rings.

Optionally, the wearable module comprises an inflatable tie, a magic tape and an inflator pump;

the detection module and the drug administration module are connected to an inner side of the inflatable tie, and the magic tape is fixed at both ends of the inflatable tie;

the magic tape is used for fixing a position of the inflatable tie after the inflatable tie is wound around the body of the user; and the inflator pump is used for inflating the inflatable tie before the detection module detects the blood glucose concentration of the user, so that the detection module and the drug administration module are closely attached to the skin of the user.

The embodiment of the present invention provides the insulin injection device, the wearable module can fix the detection module and the drug administration module to the body of the user, the detection module detects the blood glucose concentration of the user by the Raman spectrum, generates the corresponding drug administration instruction according to the blood glucose concentration, and sends the drug administration instruction to the drug administration module, and the drug administration module injects the corresponding dose of the insulin into the body of the user according to the drug administration instruction. Thus, it can be seen that after the detection module and the drug administration module are fixed to a body of a diabetic patient through the wearable module, the detection module detects the blood glucose concentration of the patient and generates the corresponding drug administration instruction, and the drug administration module injects the corresponding dose of the insulin into the body of the patient according to the drug administration instruction generated by the detection module, thus realizing automatic insulin injection according to the blood glucose concentration, and the patient does not need to remember an injection time of the insulin and manually inject the insulin, thus bringing convenience to the diabetic patient.

BRIEF DESCRIPTION OF THE DRAWINGS

In order to illustrate the technical solutions in the embodiments of the present invention or the prior art more clearly, the accompanying drawings which need to be used in describing the embodiments or the prior art will be briefly introduced hereinafter. Apparently, the accompanying drawings described hereinafter are only some embodiments of the present invention, and those of ordinary skills in the art can further obtain other accompanying drawings according to these accompanying drawings without going through any creative work.

DETAILED DESCRIPTION OF THE PREFERRED EMBODIMENTS

In order to make the objectives, the technical solutions and the advantages of the embodiments of the present invention clearer, the technical solutions in the embodiments of the present invention will be described clearly and completely hereinafter with reference to the accompanying drawings in the embodiments of the present invention. Apparently, the embodiments described are only some but not all of the embodiments of the present invention. Based on the embodiments of the present invention, all other embodiments obtained by those of ordinary skills in the art without going through any creative work belong to the scope of protection of the present invention.

Figure 1:
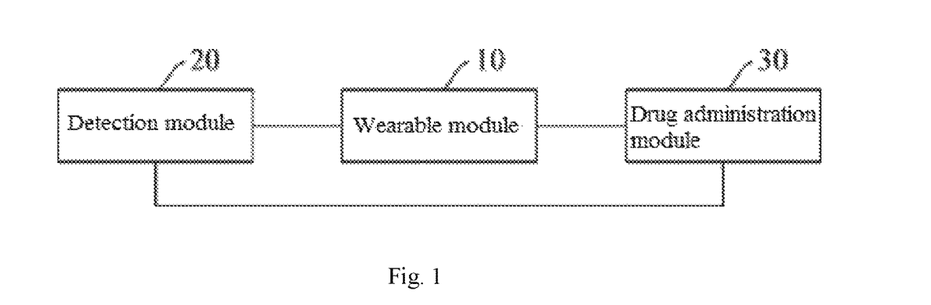
FIG. 1 is a diagram of an insulin injection device provided by an embodiment of the present invention.

As shown in FIG. 1, the embodiment of the present invention provides an insulin injection device, which can comprise a wearable module 10, a detection module 20 and a drug administration module 30.

The wearable module 10 is respectively connected to the detection module 20 and the drug administration module 30, and can be used for fixing the detection module 20 and the drug administration module 30 to a body of a user.

The detection module 20 is used for detecting a blood glucose concentration of the user by a Raman spectrum, determining a dose of required insulin according to the blood glucose concentration, generating a corresponding drug administration instruction according to the determined dose of the required insulin, and sending the generated drug administration instruction to the drug administration module 30.

The drug administration module 30 is used for storing the insulin and injecting a corresponding dose of insulin into the body of the user according to the drug administration instruction.

The embodiment of the present invention provides the insulin injection device. The wearable module can fix the detection module and the drug administration module to the body of the user, the detection module detects the blood glucose concentration of the user by the Raman spectrum, generates the corresponding drug administration instruction according to the blood glucose concentration, and sends the drug administration instruction to the drug administration module, and the drug administration module injects the corresponding dose of the insulin into the body of the user according to the drug administration instruction. Thus, it can be seen that after the detection module and the drug administration module are fixed to a body of a diabetic patient through the wearable module, the detection module detects the blood glucose concentration of the patient and generates the corresponding drug administration instruction, and the drug administration module injects the corresponding dose of the insulin into the body of the patient according to the drug administration instruction generated by the detection module, thus realizing automatic insulin injection according to the blood glucose concentration. The patient does not need to remember an injection time of the insulin and manually inject the insulin, thus bringing convenience to the diabetic patient.

Figure 2:
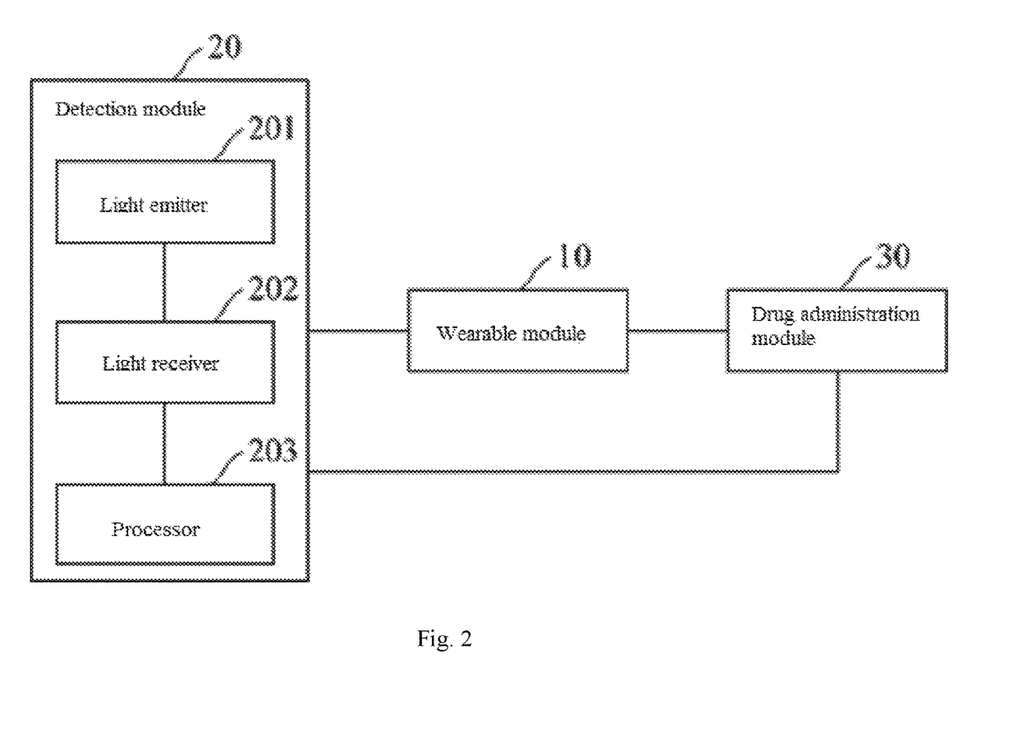
FIG. 2 is a diagram of another insulin injection device provided by an embodiment of the present invention.

Optionally, based on the insulin injection device shown in FIG. 1, as shown in FIG. 2, the detection module 20 comprised in the insulin injection device can comprise a light emitter 201, a light receiver 202 and a processor 203.

The light emitter 201 is used for emitting detection light to a subcutaneous tissue of the user through a skin of the user.

The light receiver 202 is used for receiving scattered light formed by inelastic scattering of the detection light emitted by the light emitter 201, and forming the corresponding Raman spectrum according to the received scattered light.

The processor 203 is used for determining the blood glucose concentration of the user according to the Raman spectrum formed by the light receiver 202.

The detection light emitted by the light emitter can reach the subcutaneous tissue through the skin of the user, and the detection light reaching the subcutaneous tissue undergoes the inelastic scattering under an influence of glucose molecules in blood. The scattered light formed by the inelastic scattering passes through the skin of the user and then is received by the light receiver, and the light receiver forms the corresponding Raman spectrum according to the received scattered light. Since a content of the glucose molecules in the blood can affect an intensity of the scattered light formed by the inelastic scattering, while the Raman spectrum can reflect intensity information of the scattered light, and the blood glucose concentration refers to a content of glucose in blood, the processor can determine the blood glucose concentration of the user according to the Raman spectrum formed by the light receiver.

The processor determines the blood glucose concentration of the user by the Raman spectrum formed by the light receiver, which is a non-invasive blood glucose concentration detection method. Compared with a traditional method of collecting a blood sample of the user for in vitro blood glucose concentration detection, the method does not need to pierce the skin of the user, which can not only reduce pain of the user, but also avoid infection caused during blood collection.

Specifically, the detection light emitted by the light emitter can be monochromatic light or polychromatic light emitted in a time-sharing manner. When the light emitter emits the polychromatic light, the light emitter alternately emits two or more monochromatic lights according to a set time interval. For example, the light emitter can emit a laser as the detection light through a laser device. Since an output power of the laser device is stable, the laser device can emit a laser with a stable intensity, thus ensuring an accuracy of blood glucose concentration detection.

Optionally, as shown in FIG. 2, when the processor 203 determines the blood glucose concentration of the user according to the Raman spectrum formed by the light receiver 202, the processor 203 can specifically calculate the blood glucose concentration of the user through the following formula:

$$G = \left(1 + e^{\frac{\int(Q_1 t)dt - \int(Q_2 t)dt}{\int(Q_2 t)dt + \int(Q_1 t)dt}}\right) \cdot \int(Q_2 t)dt$$

wherein, G represents the blood glucose concentration of the user, Q1 represents an intensity of scattered light formed by the detection light emitted by the light emitter 201 in a skin layer of the user, $Q_2$ represents an intensity of scattered light formed by the detection light emitted by the light emitter 201 in a subcutaneous tissue layer of the user, and t represents Raman shift of the Raman spectrum formed by the light receiver 202.

The detection light emitted by the light emitter needs to pass through the skin layer of the user to reach the subcutaneous tissue layer, and a part of the detection light undergoes the inelastic scattering in the skin layer to form corresponding scattered light. This part of the detection light can correspond to a curve on the formed Raman spectrum after being received by the light receiver. The detection light passing through the skin layer undergoes the inelastic scattering under an action of the glucose molecules in the subcutaneous tissue to form the corresponding scattered light. This part of the scattered light can correspond to another curve on the formed Raman spectrum after being received by the light receiver. Since the scattered light formed in the skin layer can be received by the light receiver prior to the scattered light formed in the subcutaneous tissue layer, the processor can identify the curve corresponding to the scattered light formed in skin layer and the curve corresponding to the scattered light formed in the subcutaneous tissue layer from the Raman spectrum formed by the light receiver.

In the Raman spectrum formed by the light receiver, a horizontal coordinate represents the Raman shift, which is namely a wave number difference between the scattered light received by the light receiver and the detection light emitted by the light emitter, and a vertical coordinate represents a number of photons, which is namely the intensity of the scattered light. In the above formula, since the Raman shift of the Raman spectrum changes continuously, a sum of products of different Raman shifts and the corresponding scattered light formed in the subcutaneous tissue can be calculated according to $\int(Q_2 t)dt$ through integral operation, and this value has a positive correlation with the blood glucose concentration G of the user.

When the detection light emitted by light emitter passes through skin layers with different thicknesses, the scattered light formed in the skin layer has different intensities. On a premise that the intensity of the detection light emitted by light emitter is low, a negative correlation exists between the intensity of the scattered light formed in the skin layer and the intensity of the scattered light formed in the subcutaneous tissue layer. Therefore, the $\int(Q_2 t)dt$ can be corrected through a correction coefficient $$1 + e^{\frac{\int(Q_1 t)dt - \int(Q_2 t)dt}{\int(Q_2 t)dt + \int(Q_1 t)dt}}$$

considering an influence of the thickness of the skin layer of the user on a blood glucose concentration detection result. It can be seen that when the skin layer on the body of the user irradiated by the detection light is thick, $\int(Q_1 t)dt$ has a relatively large value, while the $\int(Q_2 t)dt$ has a relatively small value, and at the moment, the correction coefficient has a relatively large value. The $\int(Q_2 t)dt$ with the small value is corrected through the correction coefficient, and a magnification of the $\int(Q_2 t)dt$ is increased to ensure that a small difference exists between the calculated blood glucose concentration G and a real blood glucose concentration of the user. When the skin layer on the body of the user irradiated by the detection light is thin, the $\int(Q_1 t)dt$ has a relatively small value, while the $\int(Q_2 t)dt$ has a relatively large value, and at the moment, the correction coefficient has a relatively small value. The $\int(Q_2 t)dt$ with the large value is corrected through the correction coefficient, and the magnification of the $\int(Q_2 t)dt$ is reduced to ensure that the small difference exists between the calculated blood glucose concentration G and the real blood glucose concentration of the user.

Since the thickness of the skin on the body of the user irradiated by the detection light emitted by the light emitter can affect the Raman spectrum formed by the light receiver, the intensity of the scattered light formed by the inelastic scattering of the detection light in the skin layer of the user is used as a parameter to calculate the blood glucose concentration, so that an accuracy of the blood glucose concentration calculated by the processor is ensured, thus ensuring an accuracy of the dose of the insulin injected into the body of the user by the drug administration module, and improving a safety of the insulin injection of the user.

Optionally, based on the insulin injection device shown in FIG. 2, the detection module 20 comprised in the insulin injection device further comprises a first skin tensioner.

The first skin tensioner comprises at least two fan rings, and each fan ring comprised can form an annular structure. One side of each fan ring contacting with the skin of the user is provided with an anti-skid layer.

Each fan ring comprised in the first skin tensioner moves in a direction away from a center of the annular structure before the light emitter 201 emits the detection light, so as to tension the skin of the user in an area surrounded by each fan ring, so that the light emitter 201 emits the detection light to a skin in a tensioned state.

Figure 3:
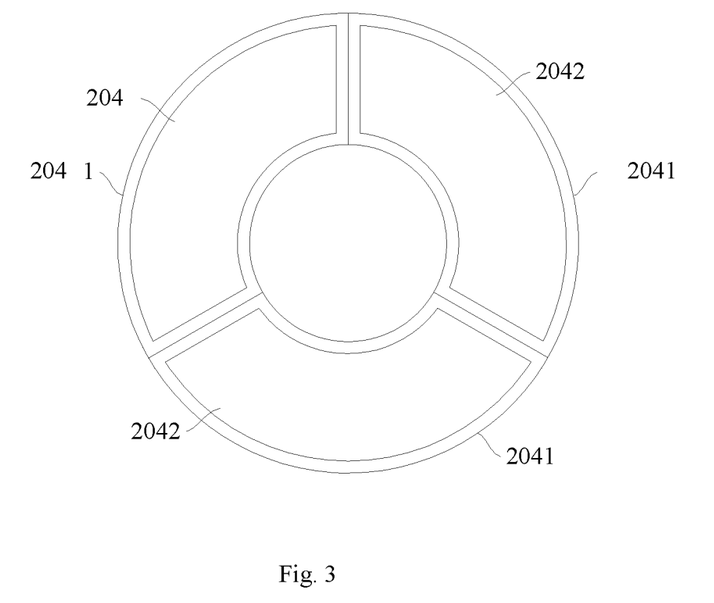
FIG. 3 is a diagram of a first skin tensioner provided by an embodiment of the present invention.
Figure 4:
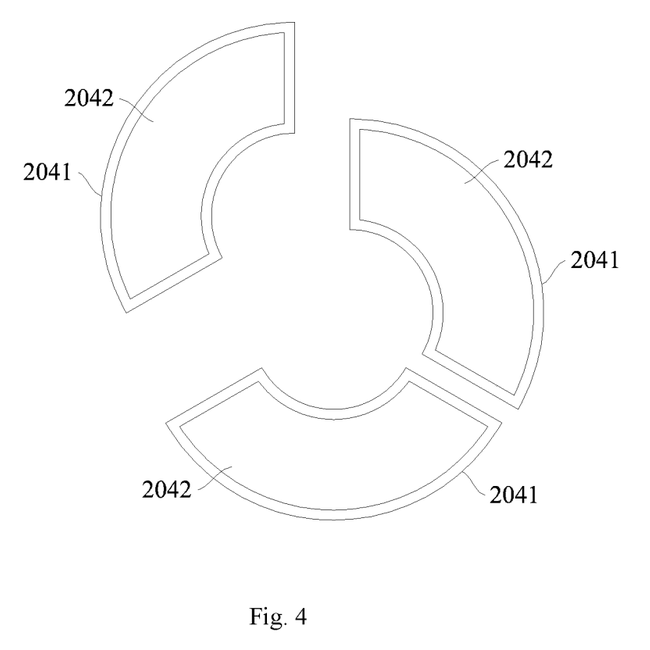
FIG. 4 is a diagram of another first skin tensioner provided by an embodiment of the present invention.

Taking the first skin tensioner comprising three fan rings as an example, as shown in FIG. 3 and FIG. 4, the first skin tensioner comprises three fan rings 2041, and one side of each fan ring 2041 is provided with an anti-skid layer 2042.

When the user fixes the detection module and the drug administration module to the body through the wearable module, the three anti-skid layers 2042 contact with the skin of the user. The three fan rings 2041 comprised in the first skin tensioner are in a state shown in FIG. 3, and the three fan rings 2041 form an annular structure. When the light emitter 201 does not emit the detection light, the first skin tensioner maintains the state shown in FIG. 3. At the moment, a skin contacting with the three anti-skid layers 2042 is in a natural state, thus ensuring that the user still has a good comfort after wearing the insulin injection device.

Before the light emitter 201 emits the detection light, the three fan rings 2041 move to a certain distance along a radial direction of the annular structure under driving of a corresponding driving mechanism, reaching the state shown in FIG. 4. When the fan ring 2041 moves in a direction away from the center of the annular structure, the anti-skid layer 2042 arranged on each fan ring 2041 is closely attached to the skin of the user. Due to a large friction between the anti-skid layer 2042 and the skin of the user, each fan ring 2041 can drive the skin in contact with the anti-skid layer 2042 arranged on the fan ring 2041 to move, so that the skin in the area surrounded by the three fan rings 2041 is tensioned. After the skin of the user is tensioned, the light emitter 201 emits single light to the skin in the tensioned state, and the light receiver 202 receives scattered light formed by the skin in the tensioned state and scattered light passing through the skin in the tensioned state (the scattered light formed in the subcutaneous tissue layer).

The first skin tensioner tensions the skin of the user, so that the light emitter emits the detection light to the skin in the tensioned state. On one hand, the skin in the tensioned state can reduce the thickness of the skin and the influence of the scattered light formed in the skin layer on the calculation of the blood glucose concentration, and improve the accuracy of the blood glucose concentration of the user calculated by the processor. On the other hand, the skin in the tensioned state is in a more stable state, which reduces an influence of a skin state change on processes of emitting the single light by the light emitter and receiving the scattered light by the light receiver, and improves the accuracy of the Raman spectrum formed by the light receiver, thus further improving the accuracy of the blood glucose concentration of the user calculated by the processor.

The anti-skid layer arranged on the fan ring can be made of a material which is compatible with a human body, such as silica gel. In order to improve the friction between the anti-skid layer and the skin of the user, a plurality of protrusions can be arranged on a surface of the anti-skid layer.

Optionally, based on the insulin injection device shown in FIG. 1, as shown in FIG. 2, the drug administration module 30 comprised in the insulin injection device can comprise at least one air tank 301, a needleless injector 302, a drug administration mechanism 303 and a drug storage mechanism 304.

The drug administration mechanism 303 is used for obtaining the corresponding dose of the insulin from the drug storage mechanism 304 according to the drug administration instruction, and adding the obtained insulin into the needleless injector 302.

Each air tank 301 is used for filling high-pressure driving gas into the needleless injector 302 after the insulin is added into the needleless injector 302 by the drug administration mechanism 303.

The needleless injector 302 is used for injecting the insulin into the subcutaneous tissue of the user in a form of liquid flow under driving of the high-pressure driving gas filled in each air tank 301.

The drug storage mechanism is used for storing the insulin. After receiving the drug administration instruction sent by the detection module, the drug administration mechanism obtains the corresponding dose of the insulin from the drug storage mechanism according to the drug administration instruction, and adds the obtained insulin into the needleless injector. The needleless injector uses the high-pressure driving gas filled in each air tank to input the insulin added by the drug administration mechanism into the subcutaneous tissue of the user in the form of liquid flow. The needle-free injector can use a principle of high-pressure spray to make a drug liquid form a thin liquid flow, which penetrates the skin instantly and reaches the subcutaneous tissue.

Firstly, the insulin is injected through the needleless injector, and the insulin is in a dispersed distribution state in the subcutaneous tissue, so that the insulin has a faster onset time and a higher absorption rate, thus controlling the blood glucose of the diabetic patient more accurately, and improving a control effect on diabetes.

Secondly, the needleless injector has no needle, so that the user has no pain or little pain, thus reducing the pain of the diabetic patient. Thirdly, since no needle is needed to repeatedly puncture an injection site, formation of induration can be avoided, thus further reducing the pain of the diabetic patient.

Figure 5:
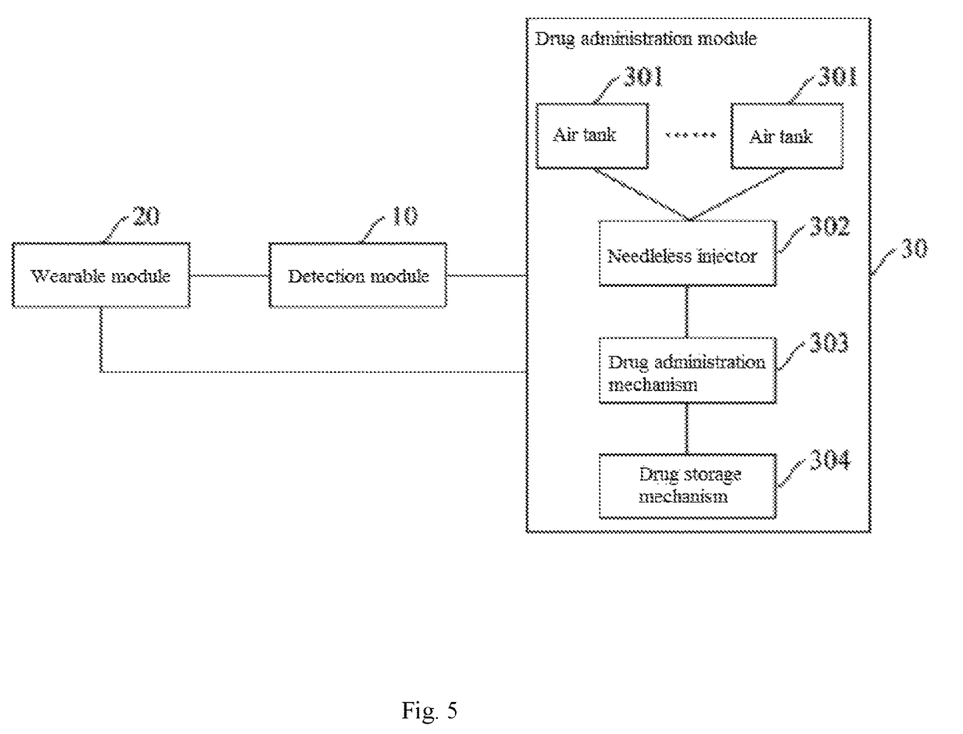
FIG. 5 is a diagram of another insulin injection device provided by an embodiment of the present invention.
Figure 6:
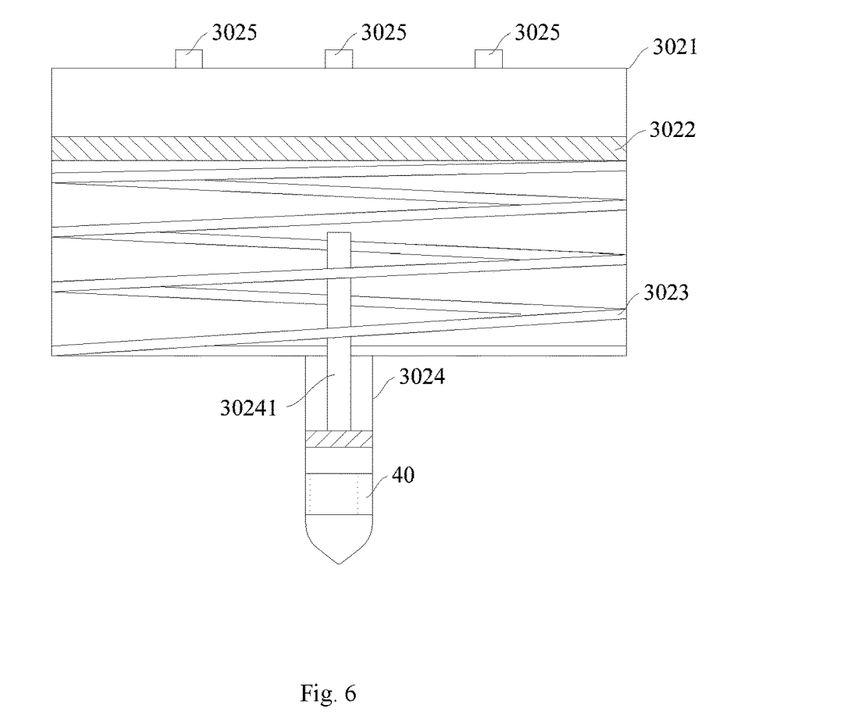
FIG. 6 is a diagram of a needleless injector provided by an embodiment of the present invention.

Optionally, based on the insulin injection device shown in FIG. 5, as shown in FIG. 6, the needleless injector can comprise a cylinder body 3021, a piston 3022, a reset spring 3023 and a piston nozzle 3024.

The cylinder body 3021 has a cylindrical structure, a first end of the cylinder body 3021 is provided with one or more air inlets 3025, and a second end of the cylinder body 3021 is provided with the piston nozzle 3024, wherein each air inlet 3025 is connected to the air tank 301 through a pipeline.

The piston 3022 is located inside the cylinder body 3021, and can reciprocate along an axial direction of the cylinder body 3021.

The reset spring 3023 is also located inside the cylinder body 3021, and is located between the piston 3022 and the piston nozzle 3024.

After the air tank 301 fills high-pressure driving gas into the cylinder body 3021 from the air inlet 3025, the piston 3022 moves in a direction close to the piston nozzle 3024 along an axis of the cylinder body 3021 under a driving action of the high-pressure driving gas. After the piston 3022 moves to contact with a piston rod 30241 of the piston nozzle 3024, an impact effect is exerted on the piston rod 30241, so that the piston rod 30241 ejects the insulin 40 in the piston nozzle 3024 in the form of liquid flow.

After the piston 3022 moves in the direction close to the piston nozzle 3024 along the axis of the cylinder body 3021 to a limit position, the compressed reset spring 3023 can drive the piston 3022 to move in a direction away from the piston nozzle 3024 along the axis of the cylinder body 3021 until the piston 3022 reaches a free position.

After the high-pressure driving gas is filled into the cylinder body by each air tank through the air inlet, the piston can impact the piston rod of the piston nozzle at a fast speed under the driving action of the high-pressure driving gas. The piston rod will push the insulin in the piston nozzle to move towards a front end of the piston nozzle at a fast speed after being impacted. The insulin is ejected from a small hole at the front end of the piston nozzle under a pushing action of the piston rod, thus ensuring that the insulin can be injected into the subcutaneous tissue of the user in the form of liquid flow. In order to facilitate a portability of the insulin injection device, a size of the needleless injector cannot be too large. Therefore, a height of the cylinder body should be controlled within a small size. However, in order to ensure that the insulin can be ejected in the form of liquid flow, the piston needs to have enough kinetic energy. Therefore, the cylinder body needs to have a large diameter. A ratio of the diameter of the cylinder body to the height of the cylinder body generally needs to be greater than or equal to 2.

Since the needleless injector is a reusable insulin injection device, the piston needs to be restored to a position away from the piston rod after the piston impacts the piston rod of piston nozzle. Therefore, the reset spring is arranged between the piston nozzle and the piston. When the piston moves in a direction close to the piston nozzle, the reset spring is compressed to store energy. After the piston moves in the direction close to the piston nozzle to a limit position, the energy stored by the reset spring is the maximum, and then the reset spring releases the stored energy to stretch, and pushes the piston to move in the direction away from the piston nozzle until the reset spring cannot continuously push the piston to move, and the piston reaches a free position. When the insulin needs to be injected for the next time, the piston can impact the piston rod of the piston nozzle under an action of the high-pressure driving gas again. In this way, the piston can reciprocate in the cylinder body under an action of the reset spring, so that the needleless injector can inject the insulin for many times.

Optionally, in the insulin injection device comprising the needleless injector shown in FIG. 6, the drug administration module can comprise at least two air tanks, and correspondingly, the first end of the cylinder body of the needleless injector can comprise at least two air inlets evenly arranged, and each air inlet is connected to one air tank through the pipeline.

In order to ensure the portability of the insulin injection device, the air tank comprised in the drug administration module has a small size. A pressure provided by the air tank with the small size is limited. In order to ensure that the high-pressure driving gas released by the air tank can drive the piston to impact the piston rod of piston nozzle at a fast speed, the high-pressure driving gas can be filled into the cylinder body by a plurality of air tanks at the same time, so that the piston is ensured to be able to obtain enough kinetic energy to impact the piston rod of piston nozzle, thus ensuring that the needleless injector can eject the insulin in the form of liquid flow. In addition, each air inlet at the first end of the cylinder body is evenly distributed, so that the high-pressure driving gas filled into the cylinder body by each air tank is evenly distributed in the cylinder body, thus ensuring that a driving force is applied by the high-pressure driving gas to the piston along an axial direction of the cylinder body, and ensuring a fluency and a stability of movement of the piston.

Figure 7:
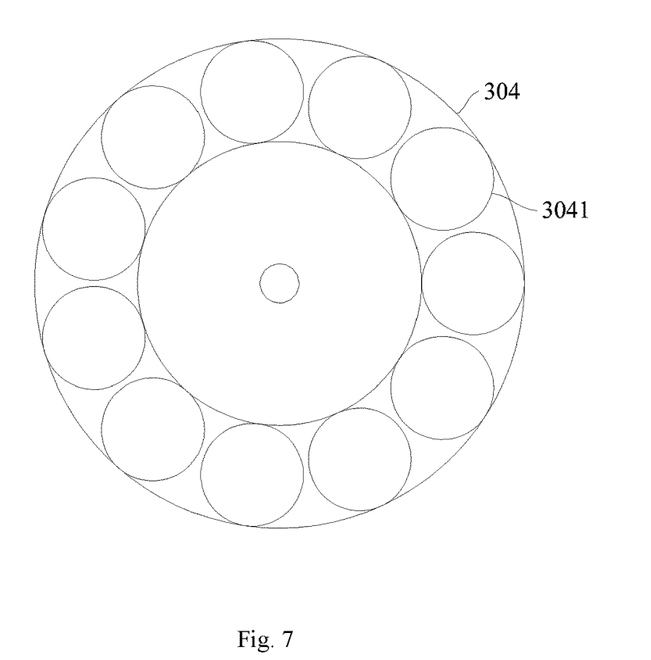
FIG. 7 is a diagram of a drug storage mechanism provided by an embodiment of the present invention.

Optionally, based on the insulin injection device shown in FIG. 5, as shown in FIG. 7, the drug storage mechanism 304 comprised in the drug administration module has a wheeled structure. A plurality of tubular drug storage bins 3041 are arranged on an inner wall of the wheeled structure, each tubular drug storage bin 3041 can store a unit dose of insulin, and the drug storage mechanism 304 can rotate along an axis of the wheeled structure under driving of the drug administration mechanism. Correspondingly, the drug administration mechanism has a rod-shaped structure. The drug administration mechanism determines the dose of the required insulin after receiving the drug administration instruction. If the unit dose of the insulin is required, the drug administration mechanism enters one tubular drug storage bin 3041 stored with the insulin, and pushes the unit dose of the insulin stored in the tubular drug storage bin 3041 into the needleless injector. If multiple unit doses of the insulin are required, the drug administration mechanism pushes the insulin stored in one tubular drug storage bin 3041 into the needleless injector, then drives the drug storage mechanism 304 to rotate by a certain angle, and enters the next tubular drug storage bin 3041, so as to push the insulin stored in the tubular drug storage bin 3041 into the needleless injector. The above steps are repeated until the dose of the insulin injected into the needleless injector is the same as that required by the drug administration instruction.

The drug storage mechanism comprises the plurality of tubular drug storage bins, and each tubular drug storage bin can store the unit dose of the insulin. In this way, the drug administration mechanism can push the insulin stored in one or more tubular drug storage bins into the needleless injector according to the drug administration instruction, so that the dose of the insulin injected into the body of the user by the needleless injector is consistent with the blood glucose concentration of the user, thus ensuring an accuracy of the dose of the insulin injected into the body of the user. The insulin stored in the tubular drug storage bin can be packed into a columnar drug package with a polymer material, and each columnar drug package contains the unit dose of the insulin. Specifically, the polymer material can be polyvinyl chloride or polypropylene. The columnar drug package can break under the pushing action of the drug administration mechanism, so that the insulin contained in the columnar drug package enters the needleless injector. In this way, a purity of a drug liquid of the insulin can be ensured by packing the insulin into the columnar drug package with the polymer material, thus preventing the drug liquid of the insulin from being polluted, and improving a safety of the insulin injection of the user.

Optionally, based on the insulin injection device shown in FIG. 5, the drug administration module 30 further comprises a second skin tensioner.

The second skin tensioner comprises a plurality of fan rings, and each fan ring can form an annular structure. One side of each fan ring contacting with the skin of the user is provided with an anti-skid layer.

The second skin tensioner can drive each fan ring to move in a direction away from a center of the annular structure before the needleless injector injects the insulin into the subcutaneous tissue of the user, so as to tension the skin of the user in an area surrounded by each fan ring.

The second skin tensioner can be the same as the first skin tensioner. A specific structure can refer to FIG. 3, FIG. 4 and the description of the first skin tensioner in the above embodiment. The second skin tensioner will not be described in detail herein.

Before the needleless injector injects the insulin into the subcutaneous tissue of the user, the second skin tensioner tensions the skin of the corresponding area of the user, and the needleless injector injects the insulin into the subcutaneous tissue of the user through the skin in the tensioned state. On one hand, after the skin is tensioned, the thickness of the skin can be reduced, and pores are expanded, so that the insulin in a liquid flow state reaches the subcutaneous tissue of the user more easily. On the other hand, the skin in the tensioned state is in a more stable state, so that relative positions of the skin of the user and the needleless injector are stable, and a direction in which the needleless injector ejects the insulin in the form of liquid flow to the skin of the user is fixed, thus ensuring a success rate of the insulin injection, and reducing the pain of the user during the insulin injection.

Figure 9:
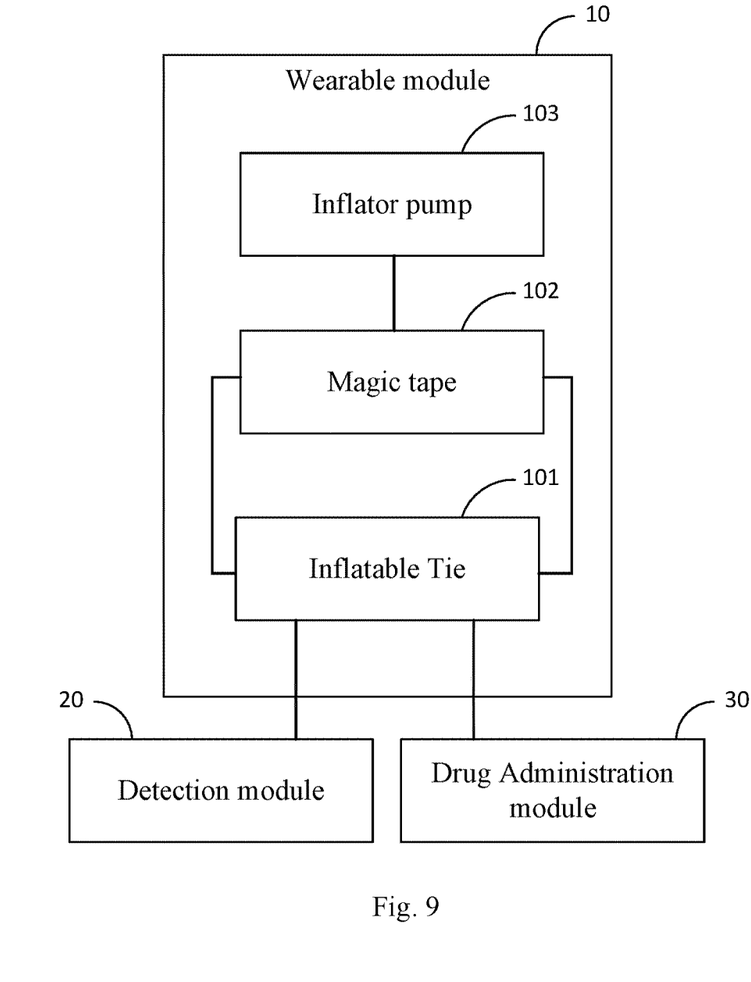
FIG. 9 is a diagram of another insulin injection device provided by an embodiment of the present invention.

Optionally, based on the insulin injection device shown in FIG. 1,101 the wearable module 10 can comprise an inflatable tie, a magic tape and an inflator pump. For example, FIG. 9 shows an embodiment of the insulation injection device with a wearable module 10 that comprises an inflatable tie 101, a magic tape 102 and an inflator pump 103.

The detection module 20 and the drug administration module 30 are both fixed on an inner side of the inflatable tie 101, and the magic tape 102 is fixed at both ends of the inflatable tie 101. The magic tape 102 can fix a position of the inflatable tie 101 after the inflatable tie 101 is wound around the body of the user. After the inflatable tie 101 is fixed to the body of the user by the magic tape 102, when the detection module 20 needs to detect the blood glucose concentration of the user, the inflator pump 103 inflates the inflatable tie 101, so that the detection module 20 and the drug administration module 30 are closely attached to the skin of the user.

Since the detection module 20 can be operated periodically, for example, the blood glucose of the user is detected once every 30 minutes, the inflator pump 103 inflates the inflatable tie 101 before the detection module 20 detects the blood glucose, so that the detection module 20 and the drug administration module 30 are closely attached to the skin of the user. After the detection module 20 detects the blood glucose once, the inflatable tie 101 can be automatically deflated. In this way, the inflatable tie 101 is inflated to ensure that the detection module 20 and the drug administration module 30 are closely attached to the skin of the user, thus ensuring an accuracy of a blood glucose detection result. After blood glucose detection is completed, the inflatable tie 101 is automatically deflated, thus ensuring that the user wearing the insulin injection device has comfortable experience.

Figure 8:
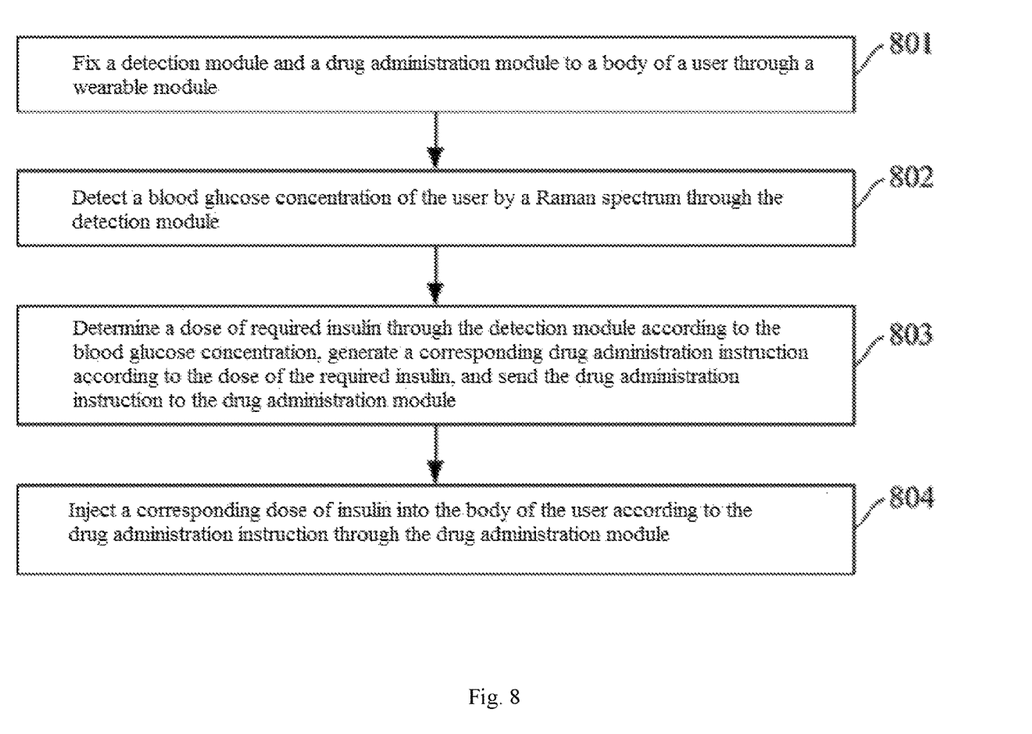
FIG. 8 is a flow chart of an insulin injection method provided by an embodiment of the present invention.

As shown in FIG. 8, an embodiment of the present invention provides a method for injecting insulin for a user by using the insulin injection device provided in any one of the above embodiments, which can comprise the following steps.

In step 801, the detection module and the drug administration module are fixed to the body of the user through the wearable module.

In an embodiment of the present invention, the blood glucose of the user with diabetes can rise after meals. Therefore, the user needs to wear the insulin injection device before meals. Certainly, the insulin injection device can also be worn for a long time. Specifically, when the user wears the insulin injection device, the detection module and the drug administration module are fixed to the body of the user through the wearable module, so that the detection module can detect the blood glucose concentration of the user, and the drug administration module can inject the insulin into the body of the user.

For example, when the wearable module comprises the inflatable tie, the magic tape and the inflator pump, the inflatable tie is wound around a abdomen or an arm of the user and directly contacts with the skin of the user, and then the position of the inflatable tie is fixed by the magic tape.

In step 802, the blood glucose concentration of the user is detected by the Raman spectrum through the detection module.

In an embodiment of the present invention, the detection module is set in advance to periodically detect the blood glucose concentration of the user. When the detection module needs to detect the blood glucose concentration of the user, the detection module detects the blood glucose concentration of the user by the Raman spectrum.

For example, when the detection module needs to detect the blood glucose concentration of the user, the inflator pump comprised in the wearable module inflates the inflatable tie, so that the detection module is closely attached to the skin of the user. The first skin tensioner comprised in the detection module tensions the skin of the user after the detection module is closely attached to the skin of the user. The light emitter comprised in the detection module emits the detection light to the tensioned skin. The light receiver comprised in the detection module receives the scattered light formed by the inelastic scattering of the detection light, and generates the corresponding Raman spectrum according to the received scattered light. The processor comprised in the detection module calculates the blood glucose concentration of the user according to the Raman spectrum generated by the light receiver through the following formula:

$$G = \left(1 + e^{\frac{\int (Q_1 t)dt - \int (Q_2 t)dt}{\int (Q_2 t)dt + \int (Q_1 t)dt}}\right) \cdot \int (Q_2 t)dt$$

wherein, G represents the blood glucose concentration of the user, $Q_1$ represents an intensity of scattered light formed by the detection light in a skin layer of the user, $Q_2$ represents an intensity of scattered light formed by the detection light in a subcutaneous tissue layer of the user, and t represents Raman shift of the Raman spectrum.

In step 803, the dose of the required insulin is determined through the detection module according to the blood glucose concentration, the corresponding drug administration instruction is generated according to the dose of the required insulin, and the drug administration instruction is sent to the drug administration module.

In an embodiment of the present invention, after the blood glucose concentration of the user is determined through the detection module, the dose of the insulin required by the user is determined according to the blood glucose concentration of the user, the corresponding drug administration instruction is generated according to the dose of the required insulin, and the drug administration instruction is sent to the drug administration module.

For example, after the detection module detects the blood glucose concentration of the user, the detection module determines the dose of the insulin corresponding to a current blood glucose concentration detection result according to a pre-defined corresponding relationship between the blood glucose concentration and the dose of the insulin. When the dose of the required insulin is not zero, the detection module generates the corresponding drug administration instruction according to the determined dose of the insulin, and sends the generated drug administration instruction to the drug administration module. When the dose of required insulin is zero, the detection module does not generate the drug administration instruction, or generates the drug administration instruction that the dose of the required insulin is zero and sends the drug administration instruction to the drug administration module.

In step 804, the corresponding dose of the insulin is injected into the body of the user according to the drug administration instruction through the drug administration module.

In an embodiment of the present invention, the drug administration module injects the corresponding dose of the insulin into the body of the user according to the drug administration instruction after receiving the drug administration instruction.

For example, after the drug administration module receives the drug administration instruction, the drug administration mechanism comprised in the drug administration module obtains the corresponding dose of the insulin from the drug storage mechanism according to the drug administration instruction, and adds the obtained insulin into the needleless injector. After the insulin is added into the needleless injector, the second skin tensioner comprised in the drug administration module tensions the skin of the user. Each air tank fills the high-pressure driving gas into the needleless injector, so that the needleless injector ejects the insulin to the tensioned skin in the form of liquid flow, thus injecting the insulin into the subcutaneous tissue of the user.

The above method for injecting insulin for the user by the insulin injection device provided in the above embodiments only comprises general steps of injecting the insulin for the user by the insulin injection device, and details of the steps can be performed according to the specific structure of the insulin injection device, which will not be described in detail herein.

To sum up, the insulin injection device provided in each embodiment of the present invention has at least the following beneficial effects.

1. In the embodiment of the present invention, the wearable module can fix the detection module and the drug administration module to the body of the user, the detection module detects the blood glucose concentration of the user by the Raman spectrum, generates the corresponding drug administration instruction according to the blood glucose concentration, and sends the drug administration instruction to the drug administration module, and the drug administration module injects the corresponding dose of the insulin into the body of the user according to the drug administration instruction. Thus, it can be seen that after the detection module and the drug administration module are fixed to the body of the diabetic patient through the wearable module, the detection module detects the blood glucose concentration of the patient and generates the corresponding drug administration instruction. The drug administration module injects the corresponding dose of the insulin into the body of the patient according to the drug administration instruction generated by the detection module, thus realizing automatic insulin injection according to the blood glucose concentration. The patient does not need to remember an injection time of the insulin and manually inject the insulin, thus bringing convenience to the diabetic patient.

2. In the embodiment of the present invention, the detection module detects the blood glucose concentration of the user by the Raman spectrum, which is a non-invasive blood glucose concentration detection method. Compared with a traditional method of collecting a blood sample of the user for in vitro blood glucose concentration detection, the method does not need to pierce the skin of the user, which can not only reduce pain of the user, but also avoid infection caused during blood collection.

3. In the embodiment of the present invention, since the thickness of the skin on the body of the user irradiated by the detection light emitted by the light emitter can affect the Raman spectrum formed by the light receiver, the intensity of the scattered light formed by the inelastic scattering of the detection light in the skin layer of the user is used as a parameter to calculate the blood glucose concentration, so that an accuracy of the blood glucose concentration calculated by the processor is ensured, thus ensuring an accuracy of the dose of the insulin injected into the body of the user by the drug administration module, and improving a safety of the insulin injection of the user.

4. In the embodiment of the present invention, the skin of the user is tensioned by the first skin tensioner before the light emitter emits the detection light. On one hand, the skin in the tensioned state can reduce the thickness of the skin and the influence of the scattered light formed in the skin layer on the calculation of the blood glucose concentration, and improve the accuracy of the blood glucose concentration of the user calculated by the processor. On the other hand, the skin in the tensioned state is in a more stable state, which reduces an influence of a skin state change on processes of emitting the single light by the light emitter and receiving the scattered light by the light receiver, and improves the accuracy of the Raman spectrum formed by the light receiver, thus further improving the accuracy of the blood glucose concentration of the user calculated by the processor.

5. In the embodiment of the present invention, the insulin is injected through the needleless injector, and the insulin is in a dispersed distribution state in the subcutaneous tissue, so that the insulin has a faster onset time and a higher absorption rate, thus controlling the blood glucose of the diabetic patient more accurately, and improving a control effect on diabetes. In addition, the needleless injector has no needle, so that the user has no pain or little pain, thus reducing the pain of the diabetic patient. Since no needle is needed to repeatedly puncture an injection site, formation of induration can be avoided, thus further reducing the pain of the diabetic patient.

6. In the embodiment of the present invention, each air inlet at the first end of the cylinder body is evenly distributed, so that the high-pressure driving gas filled into the cylinder body by each air tank is evenly distributed in the cylinder body, thus ensuring that a driving force is applied by the high-pressure driving gas to the piston along an axial direction of the cylinder body, and ensuring a fluency and a stability of movement of the piston.

7. In the embodiment of the present invention, before the needleless injector injects the insulin into the subcutaneous tissue of the user, the second skin tensioner tensions the skin of the corresponding area of the user, and the needleless injector injects the insulin into the subcutaneous tissue of the user through the skin in the tensioned state. On one hand, after the skin is tensioned, the thickness of the skin can be reduced, and pores are expanded, so that the insulin in a liquid flow state reaches the subcutaneous tissue of the user more easily. On the other hand, the skin in the tensioned state is in the more stable state, so that relative positions of the skin of the user and the needleless injector are stable, and a direction in which the needleless injector ejects the insulin in the form of liquid flow to the skin of the user is fixed, thus ensuring a success rate of the insulin injection, and reducing the pain of the user during the insulin injection.

It should be noted that, in the present invention, the relational terms such as the first and the second are only used to separate one entity or operation from another entity or operation, rather than requiring or implying practical relation or sequence of these entities or operations. In addition, the terms "comprise" and "include" or any other variant forms thereof represent non-exclusive inclusion, so that the process, method, product or device which includes a series of essentials not only include those essentials, but also include other essentials which are not listed definitely, or also include the initial essentials of the process, method, product or device. In the case that no more limitation is given, the essentials limited by the term "including . . . " do not preclude other same essentials existing in the process, method, product or device.

Those of ordinary skills in the art can understand that all or partial steps for realizing the above method embodiment can be completed by instructing related hardware through a computer program, and the above program can be stored in a computer-readable storage medium. The program can comprise the steps of the above method embodiment when executed. Moreover, the above storage medium comprises a ROM, a RAM, a magnetic disk, an optical disk, or the like, which can store program codes.

Finally, it should be noted that the foregoing is only preferred embodiments of the present invention, is only used to illustrate the technical solutions of the present invention, and is not intended to limit the scope of protection of the present invention. Any modification, equivalent substitution, improvement, and the like made within the spirit and principle of the present invention are included in the scope of protection of the present invention.

The invention claimed is:

1. An insulin injection device, comprising: a wearable module, a detection module and a drug administration module, wherein:
   the wearable module is respectively connected to the detection module and the drug administration module, and can be used for fixing the detection module and the drug administration module to a body of a user;
   the detection module is used for detecting a blood glucose concentration of the user by a Raman spectrum, determining a dose of required insulin according to the blood glucose concentration, generating a corresponding drug administration instruction according to the dose of the required insulin, and sending the drug administration instruction to the drug administration module;
   the drug administration module is used for storing the insulin and injecting a corresponding dose of insulin into the body of the user according to the drug administration instruction; and
   at least one of the detection module and the drug administration module comprising a skin tensioner, the skin tensioner comprises at least two fan rings, and the at least two fan rings configured to form an annular structure, one side of each of the two fan rings for contacting with the skin of the user is provided with an anti-skid layer, and the skin tensioner is used for driving the at least two fan rings to move in a direction away from a center of the annular structure, so as to tension the skin of the user in an area surrounded by the at least two fan rings.

2. The insulin injection device according to claim 1, wherein the detection module comprises a light emitter, a light receiver and a processor;
   the light emitter is used for emitting detection light to a subcutaneous tissue of the user through a skin of the user;

the light receiver is used for receiving scattered light formed by inelastic scattering of the detection light, and forming the corresponding Raman spectrum according to the scattered light; and the processor is used for determining the blood glucose concentration of the user according to the Raman spectrum formed by the light receiver.

3. The insulin injection device according to claim 2, wherein:

the processor is used for calculating the blood glucose concentration of the user according to the Raman spectrum through the following formula:

$$G = \left(1 + e^{\frac{\int (Q_1 t)dt - \int (Q_2 t)dt}{\int (Q_2 t)dt + \int (Q_1 t)dt}}\right) \cdot \int (Q_2 t)dt$$

wherein, G represents the blood glucose concentration of the user, $Q_1$ represents an intensity of scattered light formed by the detection light in a skin layer of the user, $Q_2$ represents an intensity of scattered light formed by the detection light in a subcutaneous tissue layer of the user, and t represents Raman shift of the Raman spectrum.

4. The insulin injection device according to claim 2, wherein the detection module further comprises the skin tensioner one side of each fan ring of the at least two fan rings for contacting with the skin of the user is provided with an anti-skid layer; and the skin tensioner is used for driving the at least two fan rings to move in the direction away from the center of the annular structure before the light emitter emits the detection light, so as to tension the skin of the user in the area surrounded by the at least two fan rings.

5. The insulin injection device according to claim 1, wherein:

the drug administration module comprises at least one air tank, a needleless injector, a drug administration mechanism and a drug storage mechanism;

the drug administration mechanism is used for obtaining the corresponding dose of insulin from the drug storage mechanism according to the drug administration instruction, and adding the obtained insulin into the needleless injector;

the at least one air tank is used for filling high-pressure driving gas into the needleless injector after the insulin is added into the needleless injector by the drug administration mechanism; and the needleless injector is used for injecting the insulin into the subcutaneous tissue of the user in a form of liquid flow under driving of the high-pressure driving gas.

6. The insulin injection device according to claim 5, wherein:

the needleless injector comprises a cylinder body, a piston, a reset spring and a piston nozzle, the cylinder body has a cylindrical structure, a first end of the cylinder body is provided with at least one air inlet, and a second end of the cylinder body is provided with the piston nozzle, wherein the air inlet is connected to the air tank through a pipeline;

the piston is located inside the cylinder body and is configured to reciprocate along an axial direction of the cylinder body the reset spring is located inside the cylinder body and between the piston and the piston nozzle;

the piston is used for moving in a direction close to the piston nozzle along an axis of the cylinder body under a driving action of the high-pressure driving gas and impacting a piston rod of the piston nozzle, so as to eject the insulin in the piston nozzle in the form of liquid flow; and the reset spring is used for driving the piston to move in a direction away from the piston nozzle along the axis of the cylinder body to a free position after the piston moves in the direction close to the piston nozzle along the axis of the cylinder body to a limit position.

7. The insulin injection device according to claim 6, wherein:

the drug administration module comprises at least two air tanks; and at least two air inlets are evenly arranged at the first end of the cylinder body, and each of the at least two air inlet is connected to a respective one of the at least two air tanks through the pipeline.

8. The insulin injection device according to claim 5, wherein:

the drug storage mechanism has a wheeled structure, at least two tubular drug storage bins are arranged on an inner wall of the wheeled structure, each tubular drug storage bin can store a unit dose of insulin, and the wheeled structure can rotate along the axis under driving of the drug administration mechanism; and the drug administration mechanism has a rod-shaped structure, is used for driving the drug storage mechanism to rotate according to the drug administration instruction, and sequentially enters at least one drug storage bin, so as to push the insulin stored in each drug storage bin into the needleless injector.

9. The insulin injection device according to claim 5, wherein:

the drug administration module further comprises the skin tensioner one side of each fan ring of the at least two fan rings for contacting with the skin of the user is provided with an anti-skid layer; and the skin tensioner is used for driving the at least two fan rings to move in the direction away from the center of the annular structure before the needleless injector injects the insulin into the subcutaneous tissue of the user, so as to tension the skin of the user in the area surrounded by the at least two fan rings.

10. The insulin injection device according to claim 1, wherein:

the wearable module comprises an inflatable tie, a magic tape, and an inflator pump;

the detection module and the drug administration module are connected to an inner side of the inflatable tie, and the magic tape is fixed at both ends of the inflatable tie;

the magic tape is used for fixing a position of the inflatable tie after the inflatable tie is wound around the body of the user; and the inflator pump is used for inflating the inflatable tie before the detection module detects the blood glucose concentration of the user, so that the detection module and the drug administration module are closely attached to the skin of the user.

11. The insulin injection device according to claim 5, wherein:

the wearable module comprises an inflatable tie, a magic tape and an inflator pump;

the detection module and the drug administration module are connected to an inner side of the inflatable tie, and the magic tape is fixed at both ends of the inflatable tie;

the magic tape is used for fixing a position of the inflatable tie after the inflatable tie is wound around the body of the user; and the inflator pump is used for inflating the inflatable tie before the detection module detects the blood glucose concentration of the user, so that the detection module and the drug administration module are closely attached to the skin of the user.

12. The insulin injection device according to claim 9, wherein:

the wearable module comprises an inflatable tie, a magic tape and an inflator pump;

the detection module and the drug administration module are connected to an inner side of the inflatable tie, and the magic tape is fixed at both ends of the inflatable tie;

the magic tape is used for fixing a position of the inflatable tie after the inflatable tie is wound around the body of the user; and the inflator pump is used for inflating the inflatable tie before the detection module detects the blood glucose concentration of the user, so that the detection module and the drug administration module are closely attached to the skin of the user.

13. An insulin injection device, comprising: a wearable module, a detection module and a drug administration module, wherein:

the wearable module is respectively connected to the detection module and the drug administration module, and can be used for fixing the detection module and the drug administration module to a body of a user;

the detection module is used for detecting a blood glucose concentration of the user by a Raman spectrum, determining a dose of required insulin according to the blood glucose concentration, generating a corresponding drug administration instruction according to the dose of the required insulin, and sending the drug administration instruction to the drug administration module; and the drug administration module is used for storing the insulin and injecting a corresponding dose of insulin into the body of the user according to the drug administration instruction;

the detection module comprises a light emitter, a light receiver and a processor;

the light emitter is used for emitting detection light to a subcutaneous tissue of the user through a skin of the user;

the light receiver is used for receiving scattered light formed by inelastic scattering of the detection light, and forming the corresponding Raman spectrum according to the scattered light; and the processor is used for determining the blood glucose concentration of the user according to the Raman spectrum formed by the light receiver;

the processor is used for calculating the blood glucose concentration of the user according to the Raman spectrum through the following formula:

$$G=(1+e^{\int f(Q_1 t)dt - \int f(Q_2 t)dt \int f(Q_2 t)dt + \int f(Q_1 t)dt}) \cdot (Q_2 t)dt$$

wherein, G represents the blood glucose concentration of the user, $Q_1$ represents an intensity of scattered light formed by the detection light in a skin layer of the user, $Q_2$ represents an intensity of scattered light formed by the detection light in a subcutaneous tissue layer of the user, and t represents Raman shift of the Raman spectrum.

* * * * *